United States Patent
Balmforth

(10) Patent No.: US 10,227,638 B2
(45) Date of Patent: Mar. 12, 2019

(54) NUCLEOTIDE POLYMORPHISM DETECTION METHOD

(71) Applicant: BASE4 INNOVATION LTD, Cambridge, Cambridgeshire (GB)

(72) Inventor: Barnaby Balmforth, Cambridge (GB)

(73) Assignee: BASE4 INNOVATION LTD., Cambridgeshire (GB)

( * ) Notice: Subject to any disclaimer, the term of this patent is extended or adjusted under 35 U.S.C. 154(b) by 131 days.

(21) Appl. No.: 15/315,482

(22) PCT Filed: Jun. 2, 2015

(86) PCT No.: PCT/EP2015/062280
§ 371 (c)(1),
(2) Date: Dec. 1, 2016

(87) PCT Pub. No.: WO2015/185564
PCT Pub. Date: Dec. 10, 2015

(65) Prior Publication Data
US 2018/0044721 A1 Feb. 15, 2018

(30) Foreign Application Priority Data
Jun. 2, 2014 (EP) ..................... 14170832

(51) Int. Cl.
*C12Q 1/6869* (2018.01)
*C12Q 1/6823* (2018.01)
*C12Q 1/6827* (2018.01)
*C12Q 1/6811* (2018.01)
*C12Q 1/6858* (2018.01)

(52) U.S. Cl.
CPC .......... *C12Q 1/6827* (2013.01); *C12Q 1/6811* (2013.01); *C12Q 1/6858* (2013.01); *C12Q 2521/501* (2013.01); *C12Q 2535/131* (2013.01); *C12Q 2561/125* (2013.01)

(58) Field of Classification Search
None
See application file for complete search history.

(56) References Cited

U.S. PATENT DOCUMENTS 5,487,972 A  1/1996  Gelfand et al.

FOREIGN PATENT DOCUMENTS

| EP | 1 602 733 | 12/2005 |
|----|-----------|---------|
| WO | 92/02638 | 2/1992 |
| WO | 97/45559 | 12/1997 |
| WO | 2005/051967 | 6/2005 |
| WO | 2006/040550 | 4/2006 |
| WO | 2008/063194 | 5/2008 |
| WO | 2013/009175 | 1/2013 |
| WO | 2013/123220 | 8/2013 |
| WO | 2014/053853 | 4/2014 |
| WO | 2014/053854 | 4/2014 |

OTHER PUBLICATIONS

Borodino et al., "Ligation detection reaction-TaqMan procedure for single nucleotide polymorphism detection on genomic DNA", Analytical Biochemistry, vol. 333, 2004, pp. 309-319.

Hashimoto et al., "Direct Detection of Mutant DNA in a Mixed Population of Higher Copy Number Wild-Type DNA Based on Ligase Detection Reaction in Conjunction with Fluorescence Resonance Energy Transfer", Analytical Sciences, 26(12):1255-1259 (2010).

Appleby et al., "New Technologies for Ultra-High Throughput Genotyping in Plants", Methods in Molecular Biology, Plant Genomics, 513:19-39 (2009).

Toubanaki et al., "Identification of Single-Nucleotide Polymorphisms by the Oligonucleotide Ligation Reaction: A DNA Biosensor for Simultaneous Visual Detection of Both Alleles", Analytical Chemistry, 81(1):218-224 (2009).

Li et al., "A colorimetric method for point mutation detection using high-fidelity DNA ligase", Nucleic Acids Research, 33(19):e168 (2005), 9 pages.

(Continued)

*Primary Examiner* — Joseph G. Dauner
(74) *Attorney, Agent, or Firm* — Wenderoth, Lind & Ponack, L.L.P.

(57) ABSTRACT

A method for characterising a DNA analyte comprised of one or more polynucleotide types characteristic of a site of nucleotide polymorphism each of which includes a target region having the formula -X-Y-Z- wherein X and Z are respectively first and second characteristic flanking oligonucleotide regions and Y is one of the variants constituting the site is provided. The method is characterised by the steps of; (a) reacting a single-stranded oligonucleotide including the target region derived from at least one of the polynucleotide types with a set of unused probes comprised of (i) a single-stranded first aptamer terminating at its 3' end in a sequence complementary to that of -X or -X-Y and (ii) one or more second single-stranded aptamers terminating at their 5' end in a sequence complementary to that of -Z-Y or -Z (as the case may be) and labelled with detectable elements which are in an undetectable state in the presence of a ligase to create a substantially double-stranded used probe comprised of the oligonucleotide, first aptamer and one of the second aptamers; (b) wholly or in part digesting the used probe with an exonuclease or polymerase exhibiting exonuclease activity in a 3' to 5' direction into its constituent single nucleotides at least one of which includes a detectable element now in a detectable state and (c) thereafter detecting the detection property associated with the now detectable element thereby identifying the nature of the Y variant and therefore the allele it gives rise to. A second mirror-image method is also disclosed. Also provided are vesicles in which the method can be carried out. The method is suitable for a range of diagnostic screening applications including the detection of mutant alleles associated with genetic disorders and cancer.

24 Claims, 1 Drawing Sheet
Specification includes a Sequence Listing.

(56) References Cited

OTHER PUBLICATIONS

Rickert et al., "Refinement of single-nucleotide polymorphism genotyping methods on human genomic DNA: amplifluor allele-specific polymerase chain reaction versus ligation detection reaction-TaqMan", Analytical Biochemistry, 330(2):288-297 (2004).
Lou et al., "Mutation detection using ligase chain reaction in passivated silicon-glass microchips and microchip capillary electrophoresis", BioTechniques, 37(3):392-398 (2004).
Myakishev et al., "High-Throughput SNP Genotyping by Allele-Specific PCR with Universal Energy-Transfer-Labeled Primers", Genome Research, 11(1):163-169 (2001).
Papp et al., "Single Nucleotide Polymorphism Genotyping Using Allele-Specific PCR and Fluorescence Melting Curves", BioTechniques, 34(5):1068-1072 (2003).
International Search Report dated Jul. 30, 2015 in International (PCT) Application No. PCT/EP2015/062280.
Written Opinion of the International Searching Authority dated Jul. 30, 2015 in International (PCT) Application No. PCT/EP2015/062280.
Extended European Search Report dated Nov. 11, 2014 in European Application No. 14170832.1.

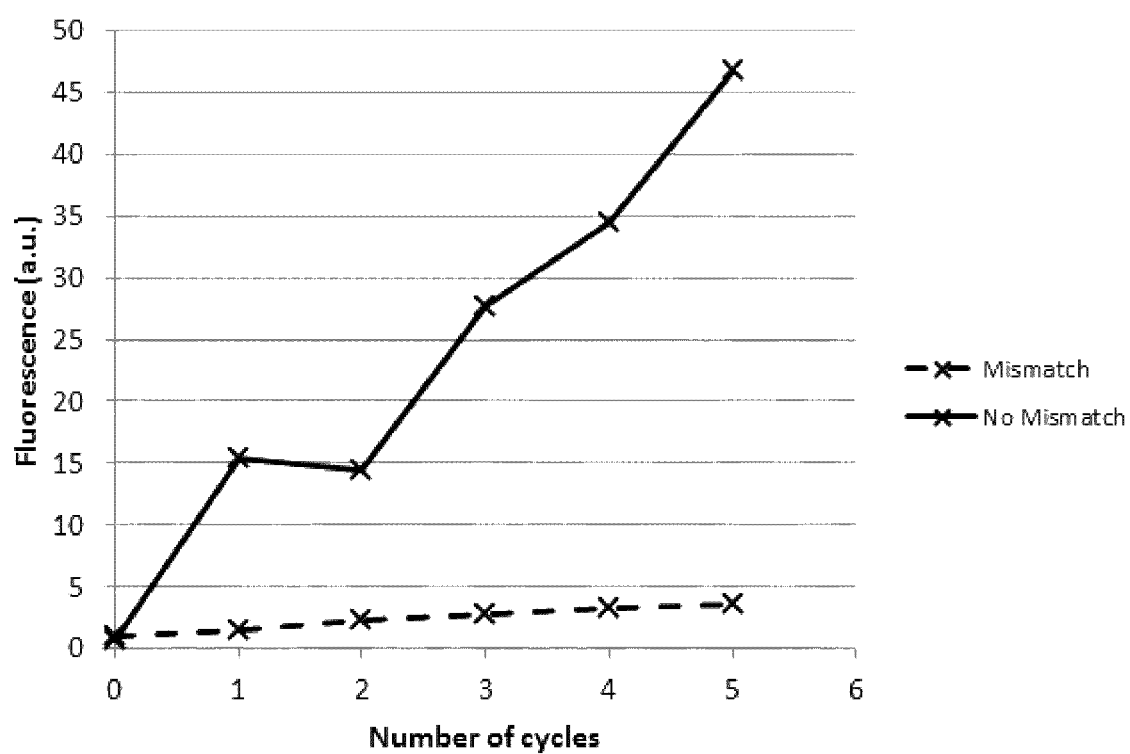

NUCLEOTIDE POLYMORPHISM DETECTION METHOD

This invention relates to a method for detecting polymorphism in a polynucleotide such as DNA.

Nucleotide variation at a given site in the sequence of a naturally-occurring DNA is a well-known phenomenon in molecular biology giving rise to polymorphic forms typically consisting of the normal or 'wild-type' allele and one or more 'mutant' forms. Common examples of this phenomenon, where the variants giving rise to the alleles are single nucleotides, are sites of single nucleotide polymorphism (SNP). To date, over fifty thousand different SNPs have been identified in the human genome and in many cases the mutations associated therewith have been found to strongly correlate with an individual's susceptibility to develop certain diseases; to be resistant to certain infections or to be intolerant to certain medicines. These observations have in turn led to significant developments in the field of medical diagnostics; for example, it is today possible to screen for malignant cancer cells by detecting the presence or absence of known associated mutant allele(s) in a biopsy from a subject. However, detection of such mutant alleles is often not straightforward given their often low occurrence relative to the wild-type in nature. This can lead to detection methods which are often complex and suffer from signal-to-noise ratio problems. There remains, therefore, a need to improve the speed, accuracy and reliability of such screening methods and the detection methods that underpin them.

A number of approaches to detecting SNPs in genetic material are used today or have been suggested in the art. One involves sequencing the whole of the allele in question but this is clearly expensive and very time-consuming. Another involves amplifying the allele using the ligase chain reaction (see for example BioTechniques (2004) 37(3) pp. 392-398). In the restriction fragment length polymorphism method, a DNA analyte is treated with a plurality of site-specific restriction endonucleases capable of cutting the polynucleotide strands only at sites where the SNP is known to occur. Thereafter by analysing the length and nature of the oligonucleotide fragments so produced the presence or absence of the SNP can be inferred. This method however suffers from the drawback of requiring multiple separation steps which are time-consuming. It is also limited by the range of endonucleases available. In another approach, the DNA analyte is treated with a pair of allele-specific probes; for example a pair of molecular beacons each having different associated fluorophores. In this method, the analyte is caused to anneal to and hybridise with its complementary probe, in the process causing the latter to emit its characteristic fluorescence. This method however suffers from single-to-noise ratio problems and the possibility of false positives especially when the frequency of occurrence of the mutant allele relative to the wild type in the analyte is very low.

In a modification of this second approach, the single to noise problems are addressed by including a step where the DNA carrying the mutant allele is amplified using the polymerase chain reaction (PCR) before it is detected. For example, in Genome Res. January 2001, 11(1) pp.163-169 and BioTechniques (2003) 34 pp.1068-1072 it has been demonstrated that polynucleotides in which mutant alleles are present can be amplified and detected using a five-component system including; (1) two allele-specific primers and a reverse primer for amplifying the two different polymorphs and (2) two differently labelled molecular beacons adapted to selectively hybridise to one or other of the two types of amplicons produced.

U.S. Pat. No. 5,487,972 teaches a process of detecting a target nucleic acid using labelled nucleotides which uses the 5' to 3' nuclease activity of a nucleic acid polymerase to cleave annealed, labelled oligonucleotide from hybridised duplexes and thus release labelled oligonucleotide fragments for detection. At column 28 it mentions the use of a probe comprised of both fluorophores and quenchers. However the method described is directed towards detecting a nucleic acid target of known sequence using a particular labelled probe rather than using a pair of probes together to distinguish between sites of polymorphism.

Appleby Methods in Molecular Biology 513 19-39 (2009) provides a review of various methods for determining single nucleotide polymorphism in plants. However there is no disclosure of the particular method we have developed which employs allele selective quenched probes systems.

EP1602733, WO 97/45559 and WO2013/009175 disclose other nucleic acid detection methods including those which involve ligation of the probe and subsequent amplification using the polymerase chain reaction.

We have now developed alternative methods for reliably identifying the variant at a given site of nucleotide polymorphism which does not rely on the use of PCR amplification. A feature of our invention is that it uses a ligase to distinguish between the alleles with a high degree of accuracy. Thus, according to a first aspect of the present invention, there is provided a method for characterising a DNA analyte comprised of one or more polynucleotide types characteristic of a site of nucleotide polymorphism each of which includes a target region having the formula -X-Y-Z- wherein X and Z are respectively first and second characteristic flanking oligonucleotide regions and Y is one of the variants constituting the site characterised by the steps of; (a) reacting, in the presence of a ligase, a single-stranded oligonucleotide including the target region derived from at least one of the polynucleotide types with a set of unused probes comprised of (i) a single-stranded first aptamer terminating at its 3' end in a sequence complementary to that of -X or -X-Y and (ii) one or more second single-stranded aptamers terminating at their 5' end in a sequence complementary to that of -Z-Y or -Z (as the case may be) and labelled with detectable elements which are in an undetectable state to create a double-stranded used probe comprised of the oligonucleotide, first aptamer and one of the second aptamers; (b) wholly or in part digesting the used probe with an exonuclease or polymerase exhibiting double-stranded exonuclease activity in a 3' to 5' direction into its constituent single nucleotides at least one of which includes a detectable element now in a detectable state and (c) thereafter detecting the detection property associated with the now detectable element thereby identifying the nature of the Y variant.

Additionally, according to a mirror-image version of this method and a second aspect of the present invention, there is provided a method for characterising a DNA analyte comprised of one or more polynucleotide types characteristic of a site of nucleotide polymorphism each of which includes a target region having the formula -X-Y-Z- wherein X and Z are respectively first and second characteristic flanking oligonucleotide regions and Y is one of the variants constituting the site characterised by the steps of; (a) reacting, in the presence of a ligase, a single-stranded oligonucleotide including the target region derived from at least one of the polynucleotide types with a set of unused probes comprised of (i) one or more single-stranded first aptamers terminating at their 3' end in a sequence complementary to that of -X or -X-Y and labelled with detectable elements which are in an undetectable state and (ii) a second single-stranded aptamer terminating at its 5' end in a sequence complementary to that of -Z-Y or -Z (as the case may be) to create a double-stranded used probe comprised of the oligonucleotide, one of the first aptamers and the second aptamer; (b) wholly or in part digesting the used probe with an exonuclease or polymerase exhibiting double-stranded exonuclease activity in a 5' to 3' direction into its constituent single nucleotides at least one of which includes a detectable element now in a detectable state and (c) thereafter detecting the detection property associated with the now detectable element thereby identifying the nature of the Y variant.

The methods of the present invention can be applied to any DNA analyte obtained from a biological source. For example, the DNA can be derived from a microbe, virus, plant or animal; especially humans and other mammals. In one preferred embodiment, the analyte is derived from a human source such as those specimens routinely collected in day-to-day medical practice such as tissue biopsies, blood samples, skin, hair, urine and sputum. In one embodiment the DNA analyte comprises the free DNA found in blood samples. This analyte will, after any necessary purification and pre-treatment (e.g. cell lysis), include the polynucleotide in the form of fragments of the original DNA known or suspected to include a site of nucleotide polymorphism. In other words, the polynucleotides of interest will then be those polynucleotide types which differ only in whether they include the wild-type or a mutant allele.

In one aspect of the invention the site of polymorphism in the polynucleotide will be one which is known to correlate with a genetic disorder or cancer so that the presence of the mutant allele will be a signifier of the existence or propensity towards developing such disease. In another aspect, the presence of this mutant allele will correlate with or be suggestive of the presence of cancerous cells allowing the method to be used for patient-screening purposes. In yet another, the polynucleotide will be derived from the DNA of a virus or microbe and the presence of the mutant allele will signify the parent organism's resistance or susceptibility to one or more medicines or vaccines. In yet another, the presence of the mutant allele will provide insights into the epidemiology of a disease. In one preferred embodiment, the site of polymorphism in the polynucleotide will be one or more SNPs and the polynucleotide will consist of the two polynucleotide types corresponding respectively to the presence of the wild-type nucleotide or a mutant nucleotide for each SNP.

The polynucleotide types which are characterised by the method of the present invention suitably include a target region of formula -X-Y-Z- wherein X and Z are respectively first and second characteristic flanking oligonucleotide regions and Y is one of the variants giving rise to the polymorphism. Generally speaking, the nucleotide sequence of the flanking regions -X- and -Z- will be known from previous sequencing studies. For the purposes of this method, these two regions will be more than two nucleotides long; preferably from 2 to 50 nucleotides, most preferably from 6 to 50 nucleotides long.

In one embodiment of the method, the single-stranded oligonucleotide including the target region is derived from its corresponding double-stranded polynucleotide by denaturation. The methods for carrying out such a denaturation are well-known in the art and may include heating the polynucleotide to its melting temperature.

In their unused state (i.e. until a given probe has been 'used' by selectively undergoing reaction with a polynucleotide), the set of probes employed in step (a) of the methods of the invention are comprised of a pair of single-stranded aptamer types. By the term 'aptamer' as used herein is meant a single-stranded nucleic acid molecule that can bind to one of the polynucleotide molecules mentioned above. In the first method described above the first aptamer type is one terminating at its 3' end in a sequence complementary to that of -X or -X-Y In the first method this aptamer type is unlabelled; in the second method it is labelled. It is the function of this aptamer type to hybridise to the oligonucleotide on the 3' side of the site of the polymorphism. In one embodiment the first aptamer(s) will be up to 100 nucleotides long, preferably 10 to 50, most preferably 10 to 20 nucleotides long. In another, it will consist only of a sequence which is the complement of -X or -X-Y. In one preferred embodiment of the first method, at least one of the nucleotides at or close to the 3' end of the first aptamer are further characterised by comprising a region resistant to exonucleolytic degradation. This can be achieved for example by modifying the linkage between the final nucleotides, preferably the final two nucleotides so that it comprises a resistant group such as phosphorothioate instead of the conventional phosphodiester. As such a phosphorothioate linkage exists in two isomeric forms; one embodiment of the invention comprises employing only the more degradation resistant of the two.

As regards the second aptamer type, this is one terminating at its 5' end in a sequence complementary to that of -Z or -Z-Y. In the first method the second aptamer type is labelled; in the second method it is unlabelled. It is the function of these aptamer(s) to hybridise to the oligonucleotide on the 5' side of the site of the polymorphism. In one embodiment the second aptamer(s) are suitably up to 100 nucleotides long, preferably 10 to 50, most preferably 10 to 20 nucleotides long. In another, it will consist only of a sequence which is the complement of -Z or -Z-Y. In one preferred embodiment of the second method, at least one of the nucleotides at or close to the 5' end of the second aptamer are further characterised by comprising a region resistant to exonucleolytic degradation. This can also be achieved, for example, by modifying the linkage between the final nucleotides, preferably the final two nucleotides so that it comprises a resistant group such as phosphorothioate instead of the conventional phosphodiester.

In one embodiment of the first and second methods, the unused probe will consist of two components being a first aptamer and a second aptamer of the relevant types defined above where Y corresponds to one of the alleles constituting the site of polymorphism. In a more preferred embodiment, however, the unused probe will be comprised of three components; either (a) the first aptamer and a pair of second aptamer types corresponding to the two different Y variants constituting the site of polymorphism in the case of the first method or (b) a pair of first aptamer types corresponding to the two different Y variants on the analyte constituting the site of polymorphism and a second aptamer (in the case of the second method). In this case, the pairs of first and second aptamer types (as the case may be) are labelled with two different types of the detectable elements discussed below; in particular two different fluorophores fluorescing at different frequencies. Finally, in both methods it is contemplated that a mixture of unused probes types can be used to identify multiple sites of polymorphism simultaneously; for example in a mixture of oligonucleotides derived from two or more polynucleotides showing different polymorphisms.

The detectable elements themselves can in principle be comprised of any elements having a characteristic detection property which can be easily detected or measured. They are also arranged on the first and second aptamer types (as the case may be) so that their associated detectable property is less detectable than when the same number of detectable elements is bound to a corresponding number of free single nucleotides.

In one preferred embodiment, the detectable elements comprise fluorophores arranged so that the second aptamer and the used probe before digestion in step (b) are essentially non-fluorescing at those typical wavelengths where the fluorophores are designed to be detected. Thus, although a fluorophore may exhibit general, low-level background fluorescence across a wide part of the electromagnetic spectrum, there will usually be one or a small number of specific wavelengths or wavelength envelopes where the intensity of this fluorescence is at a maximum. It is at or near to one or more of these maxima that essentially no fluorescence should occur. In the context of the present invention, by the term 'essentially no fluorescence' or equivalent wording is meant that the intensity of fluorescence obtained from the total number of fluorophores attached to the given aptamer type or used probe at the relevant characteristic wavelength(s) or wavelength envelope is less than 25%; preferably less than 10%; more preferably less than 1% and most preferably less than 0.1% of the corresponding intensity of fluorescence of an equivalent number of free fluorophores.

In principle, any method can be used to ensure that in the probe's unused state the fluorophores fluoresce less than when each are bound to their own free single nucleotide. One approach is to additionally attach quenchers in close proximity thereto. Another is based on the observation that when multiple fluorophores are attached to the same probe in close proximity to each other they tend to quench each other sufficiently well that the criterion described in the previous paragraph can be achieved without the need for quenchers. In the context of this patent, what constitutes 'close proximity' between fluorophores or between fluorophores and quenchers will depend on the particular fluorophores and quenchers used and possibly the structural characteristics of the oligonucleotides. Consequently, it is intended that this term be construed with reference to the required outcome rather than any particular structural arrangement on the second aptamer. However, and for the purposes of providing exemplification only, it is pointed out that when adjacent fluorophores or adjacent fluorophores and quenchers are separated by a distance corresponding to their characteristic Forster distance (typically less than 5 nm) sufficient quenching will be achieved.

Preferably each first or second aptamer (as the case may be) is labelled with up to 20, preferably up to 10 and most preferably up to 5 fluorophores. To obtain maximum advantage, it is preferred that it is labelled with at least 2 preferably at least 3 fluorophores. Consequently, ranges constructed from any permutation of these maxima and minima are specifically envisaged and therefore disclosed herein. If quenchers are employed, it is likewise preferred that the first or second aptamer is labelled with up to 20, preferably up to 10 and most preferably up to 5 of the same.

As regards the fluorophores themselves, they can in principle be chosen from any of those conventionally used in the art including but not limited to xanthene moieties e.g. fluorescein, rhodamine and their derivatives such as fluorescein isothiocyanate, rhodamine B and the like; coumarin moieties (e.g. hydroxy-, methyl- and aminocoumarin) and cyanine moieties such as Cy2, Cy3, Cy5 and Cy7. Specific examples include fluorophores derived from the following commonly used dyes: Alexa dyes, cyanine dyes, Atto Tec dyes, and rhodamine dyes. Examples also include: Atto 633 (ATTO-TEC GmbH), Texas Red, Atto 740 (ATTO-TEC GmbH), Rose Bengal, Alexa Fluor™ 750 $C_5$-maleimide (Invitrogen), Alexa Fluor™ 532 $C_2$-maleimide (Invitrogen) and Rhodamine Red $C_2$-maleimide and Rhodamine Green as well as phosphoramadite dyes such as Quasar 570. Alternatively a quantum dot or a near infra-red dye such as those supplied by LI-COR Biosciences can be employed. The fluorophore is typically attached to the first or second aptamer via a nucleotide base using chemical methods known in the art.

Suitable quenchers are those which work by a Forster resonance energy transfer (FRET) mechanism. Non-limiting examples of commercially available quenchers which can be used in association with the above mentioned-fluorophores include but are not limited to DDQ-1, Dabcyl, Eclipse, Iowa Black FQ and RQ, IR Dye—QC1, BHQ-1, -2 and -3 and QSY-7 and -21.

The first and second aptamers employed in the method of the present invention can in principle be manufactured by any of the nucleotide assembly methodologies known in the art including the H-phosphonate method, the phosophodiester synthesis, the phosphotriester synthesis and the phosphite triester synthesis. Preferred are methods employing nucleotide phosphoramadite building blocks on account of their reactivity. In these methods synthesis occurs by sequential addition of the chosen nucleotide phosphoramadite to the growing nucleotide chain at the 5' position in a cyclic four-step process involving de-blocking, coupling, capping and oxidation. The cyclic nature of this process makes it especially amenable to automation and machines to do this are readily available on the market.

Step (a) is suitably carried out by reacting the oligonucleotide, first and second aptamers, at a temperature in the range 10 to 100° C., preferably 10 to 60° C. and in the presence of a ligase. Any example of those enzymes of this type conventionally employed in the art may be employed. The ligase is preferably one which is thermostable. In one embodiment the used probe created by step (a) will be in the form of a duplex having a single-stranded overhang region at the point where exonucleolytic activity is to be initiated.

In step (b), single nucleotide monophosphates, at least one of which includes a detectable element in a detectable state, are released from the used probe by the action of an exonuclease or the exonuclease activity of a polymerase which may act in either of the 3' to 5' (first method) or 5' to 3' direction (second method). In doing so, it is important that the detectable elements present in any unused labelled aptamers are not at the same time released. The exonuclease or equivalent used in this step should therefore be one having double-stranded exonuclease activity so that only the used probe can be digested by virtue of the fact that it is longer than the unused probes and so has a higher melting temperature.

Step (b) is also suitably carried out at a temperature in the range 10 to 100° C., preferably 30 to 100° C., more preferably 50 to 100° C., even more preferably from 60 to 100° C. and most preferably between the melting temperatures of the used probe and any annealed but unreacted products. In one embodiment step (b) is carried out in the range 50 to 90° C., preferably 50 to 85° C. Examples of exonucleases or polymerases which can be used in this step include KOD, KOD HS, KOD Xstreme Hot Start, Q5, Q5 Hot Start, Phusion, Phusion HS, Dnase I (RNase-free), Exonuclease I or III (ex *E. coli*), Exonuclease T, Exonuclease V (RecBCD), Lambda Exonuclease, Micrococcal Nuclease, Mung Bean Nuclease, Nuclease BAL-31, RecJ$_f$ T5 Exonuclease and T7 Exonuclease. Preferably, the exonuclease or polymerase used in this step is one which is hot-start so that any second aptamers which have annealed to the target oligonucleotide but have not been ligated to a first aptamer are denatured before this step occurs. One net effect of step (b) is that a cascade of free single nucleotide monophosphates labelled with the detectable elements is released in which the characteristic detection property can be measured. Thus, when the used probe comprises multiple quenched fluorophores, this leads to a 'cascade' of single nucleotides labelled with fluorophores which, by virtue of them becoming separated from each other and/or any associated quenchers, are now free to fluoresce in the normal way. The observer therefore observes a growth in fluorescence signal over time.

Given that the first and second aptamers (as the case may be) used in the methods of the present invention are selective for only one allele type, one of ordinary skill will readily appreciate that detectable elements will be liberated only when an oligonucleotide comprising the particular Y allele which the labelled aptamer type is selective for is present in the reaction medium. This makes the method of the present invention especially suitable for reliably detecting minor alleles.

In one preferred embodiment of the method, step (b) continues until exonucleolytic degradation of either the whole strand associated with the first and second aptamer components of the used probe is complete or preferably that part thereof associated with the labelled aptamer if the other aptamer was designed to be resistant to exonucleolysis (see above). Ligation of fresh labelled aptamer can then occur so that either step (a) alone or steps (a) and (b) can be rendered cyclic with each cycle leading to a further release of free fluorophores. In this way, even if only low levels or a single molecule of the oligonucleotide bearing the relevant allele are present in the reaction medium, strong characteristic signals can be obtained.

Thereafter, and in step (c), the detection property associated with the detectable elements on the single nucleotides is detected. Methods of doing this are well-known in the art; for example fluorescence may be detected using a source of stimulating radiation (e.g. a laser) and a photodetector or an equivalent device tuned to the characteristic fluorescence wavelength(s) or wavelength envelope(s) of the various fluorophores. This in turn causes the photodetector to generate an electrical signal characteristic of the variant and therefore the particular allele that was present.

In a third aspect of the invention the methods defined above are carried out wholly or partially in droplets; suitably microdroplets. The advantage of this approach is that it allows numbers of individual target molecules to be counted and so to detect very low copy numbers and obtain accurate ratios of alleles. In the method of this third aspect of the invention, step (c) then preferably involves interrogating each droplet in turn to identify the detectable elements liberated and hence the nature of allele associated with the original polynucleotide type.

Suitably the microdroplets employed have a diameter of less than 100 microns, preferably less than 50 microns, more preferably less than 20 microns and even more preferably less than 15 microns. Most preferably of all their diameters are in the range 2 to 20 microns. The microdroplet version of the method can be carried out for example on a microfluidic chip.

The method of the invention is now illustrated by the following Examples.

General

For the purposes of these examples a reaction mixture containing the following components was prepared:
1 aliquot of buffer;
10 nM of each probe aptamer;
1 nM target molecule;
80 U Taq Ligase;
0.8 U Phusion II exonuclease
In this experiment the aliquot of buffer comprised:
40 mM Trizma Hydrochloride pH 8.0;
2.75 mM $MgCl_2$;
100 mM KCl;
0.5 mM DTT (dithiothreitol);
400 uM NAD (nicotinamide adenine dinucleotide);
0.01% Tween-20 (surfactant)
The probe components employed comprised the following aptamers:

```
(First aptamer)
5'-TCGTGCCTCATCGAACATG*A-3'

(Second aptamer)
5'-PCGAGGFFQFFGGTTTGTGGT-3'
``` where * is a phosphorothioate linkage, F is an Atto-655 labelled thymine base, Q is a BHQ-2 labelled thymine base and P is a 5' phosphate.

The following single-stranded oligonucleotides representing a pair of alleles characteristic of an SNP at the 26th nucleotide from the 5'end were also prepared;

```
(G allele)
5'-GTAGGTCCCACAAACCAAAAACCTCGTCATGTTCGATGAG
GCACGATAA-3'

(T allele)
5'-GTAGGTCCCACAAACCAAAAACCTCTTCATGTTCGATGAG
GCACGATAA-3'
```

The two aptamers were chosen to anneal with full complementarity to the G allele, but not the T allele because of the single nucleotide mismatch corresponding to the 5' end of the second aptamer.

EXAMPLE 1

A reaction mixture containing the G allele as the target molecule was incubated using multiple temperature cycles of 50° C. for 30 minutes followed by 70° C. for 15 minutes. At the end of each cycle the fluorescence emitted by the Atto-655 fluorophore at 629 nm after stimulation by a helium-neon laser was measured and the results expressed graphically in FIG. 1 (solid line—'No mismatch').

EXAMPLE 2

Example 1 was repeated using the T allele as the target molecule. The results are expressed graphically in FIG. 1 (dotted line—'Mismatch').

The growth in fluorescence signal for the G allele but not the T allele demonstrates the selectivity of the probe and illustrates the basis of the method of the invention for reliably distinguishing between them.

The invention claimed is:

1. A method for characterising a DNA analyte comprising one or more polynucleotide types characteristic of a site of nucleotide polymorphism each of which includes a target region having the formula -X-Y-Z- wherein X and Z are respectively first and second characteristic flanking oligonucleotide regions and Y is a different nucleotide variant characterising the site wherein the method comprises the steps of: (a) reacting one of the polynucleotide types, in the presence of a ligase, with a probe system comprised of (i) at least one single-stranded first oligonucleotide component terminating at its 3' end in a sequence complementary to that of either -X or -X-Y and (ii) at least one second single-stranded oligonucleotide components terminating at its 5' end in a sequence complementary to that of either -Z-Y or -Z, wherein one of the single-stranded oligonucleotides includes a region complementary to Y, and wherein at least one component of the probe system is labelled with at least one detectable element which is in an undetectable state to create a partially double-stranded used probe product comprised of the polynucleotide type, a first oligonucleotide component and a second oligonucleotide component; (b) wholly or in part digesting the used probe product with an enzyme exhibiting double-stranded exonuclease activity in a 3' to 5' direction into constituent single nucleotides at least one of which includes the detectable element now in a detectable state and; (c) thereafter detecting the detectable element and inferring therefrom the nature of Y.

2. The method of claim 1, wherein either step (a) alone or steps (a) and (b) is repeated in a cycle before step (c) is performed.

3. The method of claim 1, wherein the probe system of step (a) is comprised of three components comprising a first oligonucleotide component and two labelled second oligonucleotide components selective for different Y variants.

4. The method of claim 1, wherein the probe system of step (a) is comprised of three components comprising two labelled first oligonucleotide components selective for different Y variants and a second oligonucleotide component.

5. The method of claim 1, wherein the first oligonucleotide component is resistant to exonucleolytic degradation.

6. The method of claim 1, wherein the first oligonucleotide component comprises at least one phosphorothioate linkage.

7. The method of claim 1, wherein the detectable elements are fluorophores.

8. The method of claim 1, wherein the second oligonucleotide component is resistant to exonucleolytic degradation.

9. The method of claim 1, wherein the second oligonucleotide component comprises at least one phosphorothioate linkage.

10. The method of claim 1, wherein at least one quencher is associated with the detectable elements.

11. The method of claim 1, wherein the ligase is thermally stable, the enzyme exhibiting exonuclease activity is hot-start, and step (b) is carried out at a temperature in the range 60 to 100° C.

12. The method of claim 11, further comprising the step of counting the results obtained from individual microdroplets.

13. The method of claim 1, wherein the steps are carried out in microdroplets.

14. A method for characterising a DNA analyte comprising one or more polynucleotide types characteristic of a site of nucleotide polymorphism each of which includes a target region having the formula -X-Y-Z- wherein X and Z are respectively first and second characteristic flanking oligonucleotide regions and Y is a different nucleotide variant characterising the site wherein the method comprises the steps of: (a) reacting one of the polynucleotide types, in the presence of a ligase, with a probe system comprised of (i) at least one single-stranded first oligonucleotide component terminating at its 5' end in a sequence complementary to that of either -X or -X-Y and (ii) at least one second single-stranded oligonucleotide components terminating at its 3' end in a sequence complementary to that of either -Z-Y or -Z, wherein one of the single-stranded oligonucleotides includes a region complementary to Y, and wherein at least one component of the probe system is labelled with at least one detectable element which is in an undetectable state to create a partially double-stranded used probe product comprised of the polynucleotide type, a first oligonucleotide component and a second oligonucleotide component; (b) wholly or in part digesting the used probe product of step (a) with an enzyme exhibiting double-stranded exonuclease activity in a 5' to 3' direction into constituent single nucleotides at least one of which includes the detectable element now in a detectable state and; (c) thereafter detecting the detectable element and inferring therefrom the nature of Y.

15. The method of claim 14, wherein either step (a) alone or steps (a) and (b) is repeated in a cycle before step (c) is performed.

16. The method of claim 14, wherein the probe system of step (a) is comprised of three components comprising a first oligonucleotide component and two labelled second oligonucleotide components selective for different Y variants.

17. The method of claim 14, wherein the probe system of step (a) is comprised of three components comprising two labelled first oligonucleotide components selective for different Y variants and a second oligonucleotide component.

18. The method of claim 14, wherein the first oligonucleotide component is resistant to exonucleolytic degradation.

19. The method of claim 14, wherein the first oligonucleotide component comprises at least one phosphorothioate linkage.

20. The method of claim 14, wherein the detectable elements are fluorophores.

21. The method of claim 14, wherein the second oligonucleotide component is resistant to exonucleolytic degradation.

22. The method of claim 14, wherein at least one quencher is associated with the detectable elements.

23. The method of claim 14, wherein the ligase is thermally stable, the enzyme exhibiting exonuclease activity is hot-start, and step (b) is carried out at a temperature in the range 60 to 100° C.

24. The method of claim 14, wherein the steps are carried out in microdroplets.

* * * * *

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: First aptamer
<220> FEATURE:
<221> NAME/KEY: misc_feature
<222> LOCATION: (19)..(20)
<223> OTHER INFORMATION: Phosphorothioate linkage

<400> SEQUENCE: 1
tcgtgcctca tcgaacatga                                        20

<210> SEQ ID NO 2
<211> LENGTH: 20
<212> TYPE: DNA
<213> ORGANISM: Artificial Sequence
<220> FEATURE:
<223> OTHER INFORMATION: Second aptamer
<220> FEATURE:
<221> NAME/KEY: misc_feature
<222> LOCATION: (1)..(1)
<223> OTHER INFORMATION: 5' phosphate
<220> FEATURE:
<221> NAME/KEY: misc_feature
<222> LOCATION: (6)..(7)
<223> OTHER INFORMATION: Atto-655 labelled thymine base
<220> FEATURE:
<221> NAME/KEY: misc_feature
<222> LOCATION: (8)..(8)
<223> OTHER INFORMATION: BHQ-2 labelled thymine base
<220> FEATURE:
<221> NAME/KEY: misc_feature
<222> LOCATION: (9)..(10)
<223> OTHER INFORMATION: Atto-655 labelled thymine base

<400> SEQUENCE: 2
cgaggttttt ggtttgtggt                                        20

<210> SEQ ID NO 3
<211> LENGTH: 49
<212> TYPE: DNA
<213> ORGANISM: Artificial Sequence
<220> FEATURE:
<223> OTHER INFORMATION: G allele - Single-stranded oligonucleotide, SNP
      at the 26th nucleotide from the 5' end
<220> FEATURE:
<221> NAME/KEY: allele
<222> LOCATION: (26)..(26)
<223> OTHER INFORMATION: SNP

<400> SEQUENCE: 3
gtaggtccca caaaccaaaa acctcgtcat gttcgatgag gcacgataa         49

<210> SEQ ID NO 4
<211> LENGTH: 49
<212> TYPE: DNA
<213> ORGANISM: Artificial Sequence
<220> FEATURE:
<223> OTHER INFORMATION: T allele - Single-stranded oligonucleotide, SNP
      at the 26th nucleotide from the 5' end
<220> FEATURE:
<221> NAME/KEY: allele
<222> LOCATION: (26)..(26)
<223> OTHER INFORMATION: SNP

```
<400> SEQUENCE: 4
gtaggtccca caaaccaaaa acctcttcat gttcgatgag gcacgataa                49
```